(12) United States Patent
Gaines

(10) Patent No.: US 11,564,861 B1
(45) Date of Patent: Jan. 31, 2023

(54) METHOD FOR TREATING ERECTILE AND SEXUAL DYSFUNCTION WITH DUAL EXTRACORPOREAL SHOCKWAVE THERAPY

(71) Applicant: Richard Gaines, Las Vegas, NV (US)

(72) Inventor: Richard Gaines, Las Vegas, NV (US)

( * ) Notice: Subject to any disclaimer, the term of this patent is extended or adjusted under 35 U.S.C. 154(b) by 381 days.

(21) Appl. No.: 16/926,829

(22) Filed: Jul. 13, 2020

Related U.S. Application Data

(60) Provisional application No. 62/873,063, filed on Jul. 11, 2019.

(51) Int. Cl.
*A61H 23/00* (2006.01)
*A61F 5/41* (2006.01)
*A61H 19/00* (2006.01)

(52) U.S. Cl.
CPC ............ *A61H 23/008* (2013.01); *A61F 5/41* (2013.01); *A61H 19/30* (2013.01); *A61H 19/34* (2013.01); *A61H 2201/5005* (2013.01); *A61H 2205/087* (2013.01)

(58) Field of Classification Search
CPC .... A61H 23/008; A61H 2205/087; A61F 5/41
See application file for complete search history.

(56) References Cited

U.S. PATENT DOCUMENTS

| | | |
|---|---|---|
| 6,500,134 B1 | 12/2002 | Cassone |
| 7,601,127 B2 | 10/2009 | Schuitheiss et al. |
| 9,381,380 B2 | 7/2016 | Ein-Gal |
| 9,913,748 B2 | 3/2018 | Spector et al. |
| 2012/0239055 A1 | 9/2012 | Spector et al. |
| 2015/0182416 A1 | 7/2015 | Forsell |
| 2016/0051437 A1 | 2/2016 | Forsell |
| 2017/0258676 A1 | 9/2017 | Lue et al. |
| 2017/0296427 A1 | 10/2017 | Warlick et al. |
| 2018/0147111 A1 | 5/2018 | Gaines |
| 2018/0228638 A1 | 8/2018 | Spector et al. |

OTHER PUBLICATIONS

Storz Medical ("Duolith SD1 ultra—Shock wave system" accessed online on Sep. 23, 2022; available online Nov. 28, 2018 https://web.archive.org/web/20181128110309/https://www.storzmedical.com/disciplines/orthopaedics/product-overview/duolith-sd1-ultra.html) (Year: 2018).*

* cited by examiner

*Primary Examiner* — Kaylee R Wilson
(74) *Attorney, Agent, or Firm* — The Patent Professor

(57) ABSTRACT

A medical procedure for treating human male and female patients suffering from erectile or sexual dysfunction, respectively, with extracorporeal dual shockwave therapy applied to strategic, gender-specific anatomical regions to improve sexual function. Some or all of the gender-specific anatomical regions may be anesthetized using a topical or local anesthetic, and both radial and focused extracorporeal shockwaves are applied to the anatomical regions at predetermined bar values, frequencies, and number of shockwave pulses, based on the severity of the sexual dysfunction. Radial and focused extracorporeal shockwaves may be used in additional to convention methods of treating both erectile and sexual dysfunction.

20 Claims, 10 Drawing Sheets

METHOD FOR TREATING ERECTILE AND SEXUAL DYSFUNCTION WITH DUAL EXTRACORPOREAL SHOCKWAVE THERAPY

CROSS-REFERENCE TO RELATED APPLICATIONS

This application claims the benefit of U.S. Provisional Patent Application Ser. No. 62/873,063, filed on Jul. 11, 2019, which is incorporated by reference herein in its entirety.

FIELD OF THE INVENTION

The present invention relates to medical methods or procedures, and more particularly, to a medical procedure using dual, i.e., radial and focused extracorporeal shockwave therapy (ESWT) for treating strategic, gender-specific anatomical regions of both males and females suffering from erectile and sexual dysfunction to improve sexual health function.

BACKGROUND OF THE INVENTION

Medical professionals are generally in agreement that healthy sexual function helps nurture both the physical and emotional attributes of humans in both males and females. Scientific evidence has demonstrated the benefits of having a healthy sex life some of which include having less stress and tension, sleeping better, increasing self-esteem, and having a more positive outlook on life. It is generally well-known that healthy sexual function is typically associated with diet, and both the physical and mental state and condition of the individual participants. Because sexuality is often a reflection of one's general state of health, it is important for individuals to watch their diet to maintain a healthy weight, avoid smoking, and limit the intake of alcohol, as these are all factors that impact one's ability to engage in healthy sexual activity. However, there are circumstances where life style management alone is simply not enough to maintain good sexual health often as a result of illness, a medical condition, or other pathological factors.

One known medical condition that often compromises a male's sexual health is erectile dysfunction, known or commonly referred to as ED. Erectile dysfunction involves the inability to acquire, or retain an erection that is deemed firm enough to engage in sexual activity, and affects millions of male individuals worldwide. The inability to engage in sexual activity not only taxes the individual's self-worth and dignity, but limits a person's desire and capability of engaging in consensual sexual activity. As a result of such sexual dysfunction, many individuals prefer to disassociate themselves from circumstances that may impose or solicit sexual desire. There are a variety of medical conditions that are commonly known to cause erectile dysfunction in males. For example, studies have shown that male individuals who suffer from diabetes, depression or mental illness, obesity, or cardiovascular disease including high blood pressure, are strong candidates for experiencing erectile dysfunction. Individuals suffering from such medical conditions, often take prescription medication that typically impose side effects that impedes sexual function or desire. As such, individuals find themselves in a balancing act of taking prescribed medications to manage medical health conditions on one hand, while compromising sexual function and experiencing erectile dysfunction on the other as a result of prescription medication side effects. For this reason, patients must resort to seeking the proper solutions and treatments that are needed to overcome erectile dysfunction in an effort to achieve acceptable levels of healthy, sexual function. Sexual dysfunction does not only occur in males, but in females as well. Females experience sexual dysfunction in a variety of different ways. For example, sexual dysfunction in females is often characterized as having sexual pain or orgasmic disorders, or having low sexual desire, or sexual arousal. In this regard, both males and females can experience sexual dysfunction, which if left untreated, can impact their ability to engage in healthy, sexual activity.

Advancements in medical therapies and prescribed medicines have provided limited benefits in treating sexual dysfunction including erectile dysfunction. Some patients have resorted to conventional group therapy, or one-on-one counseling to address underlying psychological conditions that may be the cause of sexual dysfunction. Others have turned to a first-line of therapy for treating physical conditions of sexual dysfunction by using oral medication, such as phosphodiesterase type 5 inhibitors (PDE5I) often referred to as Viagra or Cialis. The PDE5I medication is prescribed to enhance the effects of nitric oxide to relax the muscles in the penis while promoting blood flow. Still other second-line therapies entail the use of intra-cavernosal injections with vasodilating agents such as Caverject Impulse. Such treatments are typically taken on demand prior to engaging in sexual activity as they do not alter the underlying pathophysiology of erectile tissue. In situations where erectile dysfunction is more severe, or in cases where individuals do not respond well to PDE5I or injection therapy, alternative modes of treatment include penis pumps, penile implants including inflatable pumps, or other penile prosthesis or implants to address severe pathological changes in the penis. However, penile implants typically entail more invasive surgeries that require patient monitoring, pain management, pose greater risks of infection, and may often lead to complications during use. Other avenues of treatment also include testosterone replacement therapy, or Alprostadil urethral suppository therapy, or use of exosomes. Prescribed methods of treating female sexual dysfunction often involves the use of estrogen or androgen therapy, and ospemifene, bremelanotide and fibanserin medications, all of which have particular side effects that may discourage use and medical management.

Other advanced methods of treatment have been developed to help improve sexual function in patients in light of various drawbacks provided by the conventional therapy of oral or injection medications, psychological therapy, and invasive surgeries for implantation of penile prosthesis. One therapeutic approach involves the combinational use of a platelet rich plasma procedure and the application of radial extracorporeal shockwave therapy (ESWT). Although radial ESWT is found beneficial for plantar fasciitis, a common cause of heal pain, there exists little to no medical or academic research, studies or empirical evidence or data that supports the effectiveness of using radial ESWT for the treatment of erectile dysfunction. Pronounced patient satisfaction in undergoing radial ESWT for erectile dysfunction remains in flux and questionable at best.

Accordingly, there exists a need to solve at least one of the aforementioned problems mentioned herein, and to provide an effective, non-invasive medical procedure for treating females and males suffering from sexual and erectile dysfunction to improve sexual health function, while overcoming the deficiencies associated with conventional methods of treatment involving PDE5Is, intra-cavernosal injections, invasive surgical implants, and solely radial extracorporeal shockwave therapy (ESWT).

SUMMARY OF THE INVENTION

The present invention is directed to a medical procedure for improving sexual function in human patients. The medical procedure includes treating strategic, gender-specific anatomical regions of male and female genitalia with radial and focused extracorporeal shockwave therapy (ESWT) at prescribed bar values, frequencies, and shockwave amounts, to promote production of new vasculature, blood circulation and cell growth to treat sexual and erectile dysfunction and improve sexual health function.

A first embodiment of the invention provides a medical procedure for treating human patients suffering from sexual dysfunction, the medical procedure comprising: soliciting responses to sexual health questions associated with human male and female patients, where the sexual healthcare questions are provided in a sexual health questionnaire; determining a level of severity of the sexual dysfunction based on the responses; optional anesthetizing strategic gender-specific regions of either the male or the female patient, and applying extracorporeal dual shockwave therapy including focused and radial shockwaves to strategic gender-specific regions of the male or female patient based on the determined level of severity of the sexual dysfunction using an extracorporeal focused and radial shockwave generator system.

In one aspect, the sexual health questionnaire comprises a first sexual health questionnaire specifically designed for females, and a second sexual health questionnaire specifically designed for males.

In another aspect, determining the level of severity of sexual dysfunction includes associating a first number of dual shockwave treatments for severe sexual dysfunction, a second number of dual shockwave treatments for moderate sexual dysfunction, and a third number of dual shockwave treatments for mild sexual dysfunction.

In yet another aspect, the step of optional anesthetizing strategic gender-specific regions includes anesthetizing strategic anatomical regions of the male patient including the penile shaft, and perineal areas including the corpora cavernosa, crura, pudendal, or bulbospongiosis. The step of anesthetizing may include applying a topical or local anesthetic to the strategic anatomical regions of the male.

In another aspect of the invention, the step of optional anesthetizing strategic gender-specific regions further includes anesthetizing strategic anatomical regions of the female including the anterior vaginal wall, and portion of the vulva including perineal areas of the corpora of clitoris, the crura, labia majora, the labia minora (pudendal region), and the median raphe and perineum. The step of anesthetizing may include applying a topical or local anesthetic to the strategic anatomical regions of the female.

In another aspect, the step of applying extracorporeal dual shockwave therapy including focused and radial shockwaves to the strategic gender-specific regions of said male includes applying focused shockwaves at a value of about 0.20 to about 0.35 mJ/mm$^2$@4 Hz, for a total of about 1600 to about 3600 pulses, and applying radial shockwaves at a value of about 1.7 to about 3.0 bars, which correlates to about 0.15 to about 0.30 mJ/mm$^2$@15 Hz for about 4500 to about 6500 pulses.

In another aspect, the step of applying extracorporeal dual shockwave therapy including focused and radial shockwaves to the strategic gender-specific regions of said female includes applying focused shockwaves at a value of about 0.25 to about 0.35 mJ/mm$^2$@4 Hz, for about 1600 to about 3600 pulses, and applying radial shockwaves at a value of about 1.7 to about 3.0 bars, which correlates to about 0.15 to about 0.30 mJ/mm$^2$@15 Hz for about 4500 to about 6500 pulses.

In one aspect, the step of applying extracorporeal dual shockwave therapy including focused and radial shockwaves to the strategic gender-specific regions including providing up to 12 treatments for severe sexual dysfunction, up to 6 treatments for moderate sexual dysfunction, and up to 3 treatments for mild sexual dysfunction.

In another aspect, a further step includes providing post-treatment medical instructions to either the male or female patients upon completing the step of applying extracorporeal dual shockwave therapy including focused and radial shockwaves.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower". "left", "rear". "right", "front", "back", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed to a medical procedure for treating both male and female patients with radial and focused extracorporeal shockwave therapy (ESWT) applied to strategic, gender-specific anatomical regions for treating sexual and erectile dysfunction to improve sexual function. As used throughout the description, it will be understood that the term. "extracorporeal" means shockwaves that are generated externally to a patient's body, and transmitted from a coupling medium through a patient's skin.

Figure 1A:
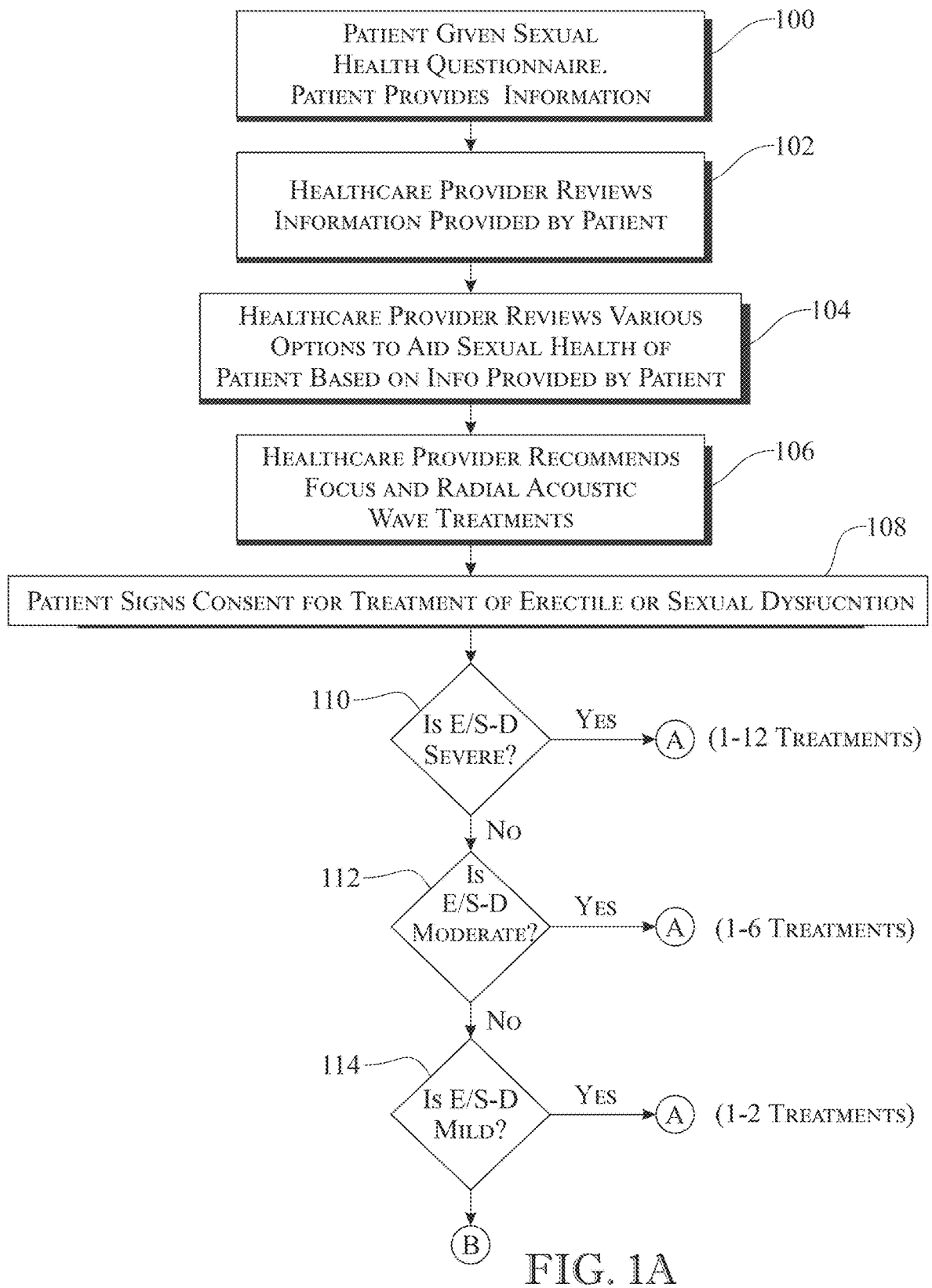
FIGS. 1A and 1B present flow charts illustrating a medical procedure showing the steps of soliciting and evaluating sexual health questions for male and female patients, and determining treatment options including extracorporeal dual shockwave therapy for treating sexual dysfunction to improve sexual function, in accordance with one embodiment of the present invention.
Figure 1B:
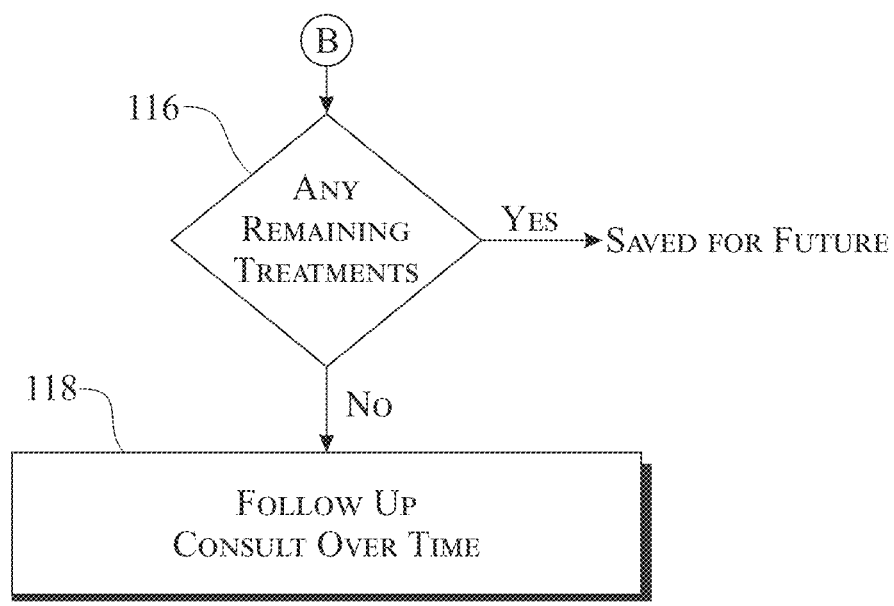

Referring now to FIGS. 1A and 1B, there are shown flow charts illustrating a medical procedure including the steps of soliciting sexual health questions from patients and evaluating the responses, in addition to other medical information, to treat males and females suffering from sexual dysfunction with dual extracorporeal shockwave therapy (ESWT) to improve sexual health function, in accordance with one embodiment of the present invention. The prescribe medical procedure of treating patients with sexual dysfunction begins with the initial step 100 of consulting with patients and soliciting sexual health information that is evaluated by the attending physician to determine the correct medical therapeutic approach needed to treat sexual dysfunction in both males and females. The patient is given a sexual health questionnaire that is tailored to solicit information relating to the sexual context of a person, and includes a host of medical questions that will be used to provide gender-specific therapy. For example the sexual health questionnaire may be formulated to solicit information such as, but not limited to, a patient's profile information, sexual activity, medical history, sexual deficiencies, information on any historical surgeries, medical treatments acquired, use of hormone therapy, types of medications patient is taking, whether the person suffers from any psychological or physical condition, whether the patient has any particular allergies to medications or foods, and any other medical information or data that will be considered to help the attending physician determine whether the patient is suffering from erectile or sexual dysfunction, and if so, the severity of the dysfunction. The sexual healthcare questions are gender-specific, for example with males, sexual healthcare questions may be specifically geared to gathering information on erectile dysfunction, while for female patients, the sexual healthcare questions may be tailored to determine whether the female suffers from low sexual desire, sexual arousal disorder, orgasmic disorder, or sexual pain disorder. As such, the sexual health questionnaire is formulated to solicit information specifically from both males and females, where in some cases, the questions may be identical in nature but obviously different regarding specific anatomical features and function. In one embodiment, the sexual health questionnaire may be characterized as sexual health inventory for men (SHIM), and female sexual function inventory for females (FSFI). As such, the SHIM questionnaire is used by the attending physician to identify and determine whether male patient suffers from erectile dysfunction and if so, the severity of the affliction, while the FSFI is used to identify and determine whether female patients suffer from sexual dysfunction, and if so, the type and severity of the sexual dysfunction.

Upon completing the sexual health questionnaire, the responses are carefully reviewed and analyzed, in step 102. The attending physician may request other tests the help further determine the underlying root cause of the sexual disorder. For example, the attending physician may order blood tests, perform a physical exam, consult with other physicians, ask the patient questions regarding general psychological conditions of the patient, discuss the patient's diet, types of medications used by the patient, and consider a broad range of medical data and information to better determine the level of severity of sexual dysfunction. The gathered responses to the sexual healthcare questionnaire and the medical data and information from other sources like lab results, is then used to calculate or determine a designated sexual function score that is used by the attending physician to determine the type and severity of sexual dysfunction of each patient.

In step 104, the physician then discusses the analyzed results with the patient and presents therapeutic treatment options to the patient while explaining the benefits and risks associated with the various treatment options available. The attending physician will consider using a variety of therapies to treat sexual dysfunction including, platelet-rich plasma (PRP) procedure, Wharton's jelly, exosome therapy, peptides, hormone therapy, intra-corporeal injections, hyperbaric oxygen therapy, pulsed electromagnetic field therapy, or use of PDE5 medications, penal implants, and/or psychological therapy. With the advent of proven results and overall patient satisfaction in mind, and upon determining that the patient will likely be non-responsive to conventional therapies, in step 106, the healthcare provider will recommend extracorporeal dual shockwave therapy (ESWT) comprising both radial and focused acoustic shockwaves to the patient. Upon careful review, and discussion with the attending physician, and after weighing the risks and benefits involved with dual shockwave therapy, the patient makes an informed decision, and fills out a patient consent form for receiving radial and focused extracorporeal shockwave therapy (ESWT), as illustrated at step 108.

Based on the responses to the sexual health questionnaires (SHIM) and (FSFI), the sexual functions scores, results of the blood work, physical exam, and other pertinent medical information and data, the attending physician determines the level of severity of both the male's erectile dysfunction, or the female's sexual dysfunction, to strategize the requisite number of dual shockwave treatments needed to effectively treat the patient's sexual dysfunction. As such, in step 110, the attending physician will determine whether the patient's erectile or sexual dysfunction (E/S-D), is severe. Upon determining the patient's sexual dysfunction is severe, the attending physician will then recommend anywhere from 1 to 12 treatments of dual shockwave therapy. In step 112, if the sexual dysfunction is determined to be moderate, the recommendation is for the patient to undergo 1 to 6 dual shockwave treatments, and in step 114, if the sexual dysfunction is mild, then the patient will require fewer dual shockwave treatments, such as, 1 to 3 treatments. It is understood that, the number of treatments required in both males and females, may correlate to or depend on, the sexual health index scores that was determined in association with responses to the sexual health questionnaire (SHIM/FSFI), and any results of medical tests, and physical evaluation and examination made by the attending physician. In one exemplary embodiment, a SHIM/FSFI score of less than 13, signifies a need of up to about 12 treatments, e.g., about 6 to 12 treatments, a SHIM/FSFI score of between 14 to 18, signifies a need of up to about 6 treatments, e.g., about 3 to 6 treatments, and a SHIM/FSFI score of between 19 to 22 may signify a need of about 1 to 3 treatments. It is understood that the number of treatments given to each patient may be increased or decreased as needed. For example, a SHIM/FSFI score of less than 13 may mean that the patient will require up to 15 treatments, or up to 20 treatments, or up to 7 treatments. As such, the number of shockwave treatments associated with SHIM/FSFI scores, may be increased, or decreased, to provide effective dual shockwave therapy to both males and females suffering from sexual dysfunction. The term, "treatment(s)" as used herein, may include a set number of, or a set group of, radial and focused shockwaves per a defined bar, or group of defined bar values, (a specified pressure magnitude, or a group of specified pressure magnitudes), at the same or different frequency, and any combination thereof.

As provided in step 116, at any time during the treatments, if the patient responds well to treatment, and is deemed to be in satisfactory condition, and the attending physician believes that no further radial and focused extracorporeal shockwave therapy (ESWT) is needed, than the patient is given the option to reserve unused treatments for a future date if needed. Alternatively, if all radial and focused extracorporeal shockwave (ESWT) treatments have been given and used by the patient, the attending physician will recommend a follow-up appointment at some prescribed date and time to reexamine the patient and discuss whether any further treatments should be considered, as noted in step 118 in FIG. 1B. During the follow-up appointment, the patient may be required to take another sexual health questionnaire, and undergo additional medical tests or exams, to determine a new protocol of shockwave therapy, whether alone, or in combination with conventional therapies such as the use of PDE5 medication, hormone therapy, exosomes, or injections.

Figure 2:
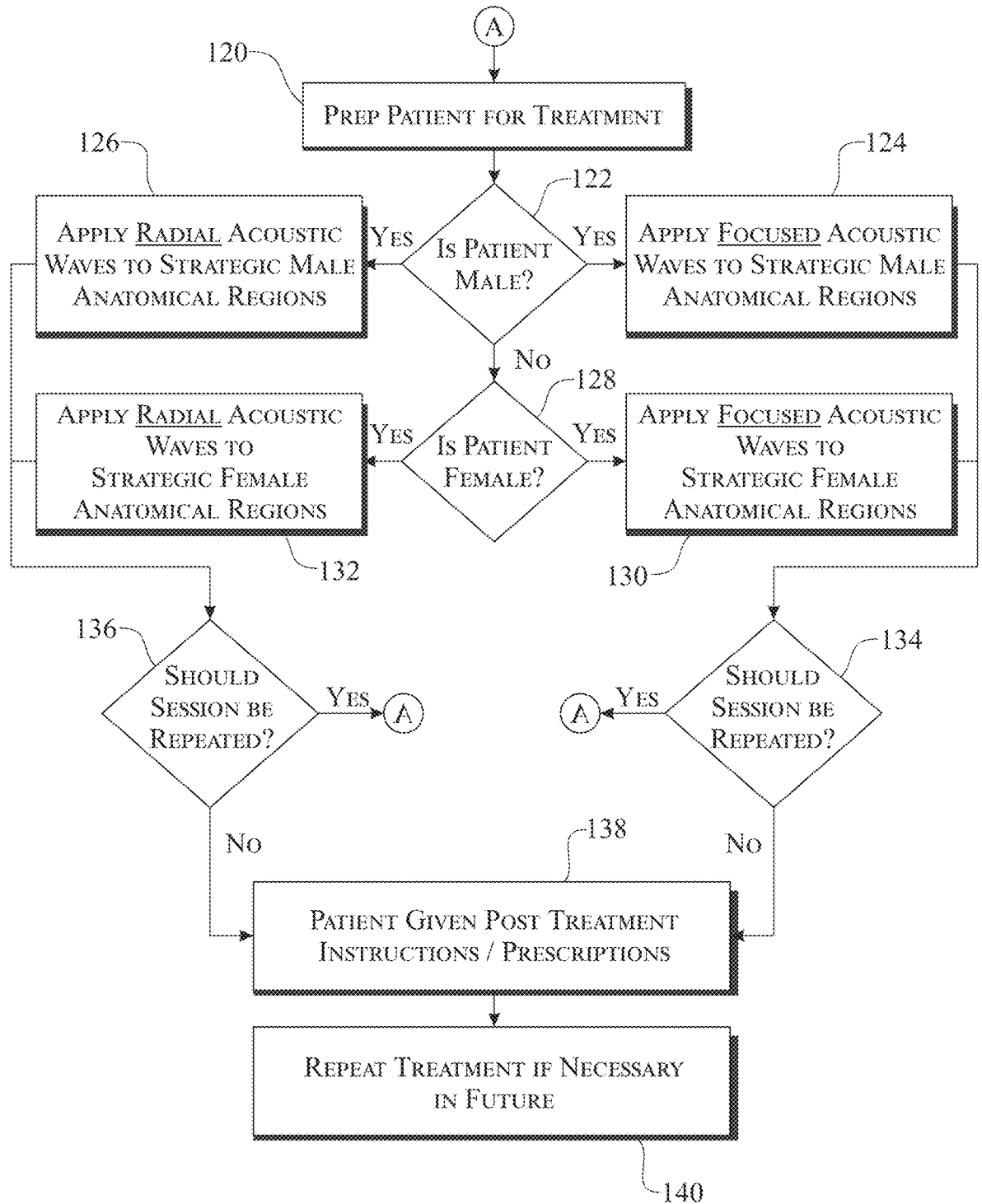
FIG. 2 presents a flow chart illustrating the medical procedure showing the steps of treating both male and female patients suffering from erectile and sexual dysfunction, respectively, with extracorporeal dual shockwave therapy to improve sexual function.
Figure 3:
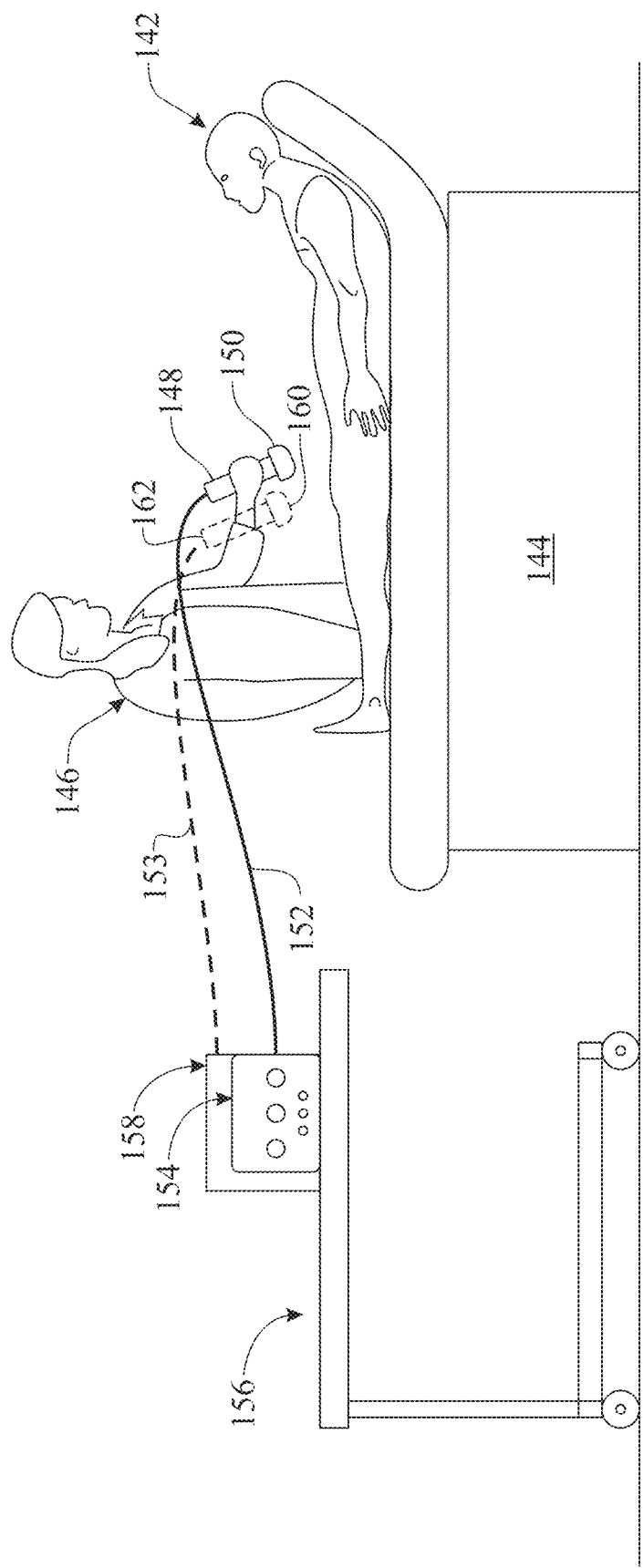
FIG. 3 presents an operative view of a physician holding a handheld probe coupled to a focused and radial shockwave generator to readily treat male and female patients suffering from sexual dysfunction with dual shockwave therapy to improve the patient's sexual health, showing a patient in a supine position on a medical bed.

Turning now to FIG. 2, there is shown a flow chart illustrating the medical procedure for treating patients suffering from erectile or sexual dysfunction with extracorporeal dual shockwave therapy (ESWT) comprising both radial and focused acoustic shockwaves. In step 120, the treatment process begins by properly preparing the patient for dual shockwave therapy. The patient, generally denoted at 142, is invited to the procedure room, and given instructions to lower or remove the clothing covering the genitalia, and to lie in a supine or semi-reclined position on a medical procedure table or bed 144, as best illustrated in FIG. 3. All patients are treated in the upmost professional and dignified manner during all stages of medical dual shockwave treatment, and the procedure is conducted under sterile conditions. In keeping with a patient's dignity, preventing embarrassment, and reducing psychological impact, the patient's genital region is covered during any pause of therapy or treatments with a garment, sheet or towel. Gender-specific anatomical regions of interest in both the male and female patient are appropriately anesthetized to lessen any pain or discomfort during the procedure.

With regard to males, the male's penis is drawn out of the prepuce. An attending assistant may be instructed to shave the lower abdomen or groin area of the patient if needed. A topical or local anesthetic, or numbing cream or gel, is applied to the shaft of the male penis, and the perineal region. To be more specific, in a male, an anesthetic cream may be applied to parts of, or the entire region of, the shaft of the penis, or gross anatomical regions attributed to the corpora cavernosa, crura, pundendal, or bulbospongiosis regions. It will be understood that the topical anesthetic, or numbing cream or gel is generally applied to areas or regions in which the shockwave applicator probe 150, 160 will come into contact with the strategic anatomical regions over the skin of the patient. As such, the anesthetic, and numbing cream may be applied to the perineal and/or perineum regions of both the male or female patient. The anesthetic or numbing cream may comprise any topical or local anesthetic that is well-known in the medical arts. For example, in one embodiment the anesthetic may comprise a lidocaine solution that is injected for example, in the penile nerves of the penis. With females, the lidocaine solution may be injected in the clitoral nerve. As such, the lidocaine solution is applied to the strategic, anatomical regions as illustrated in FIGS. 4 through 9, for both male and female patients. It is appreciated that applying an anesthetic to either or both males and females is an optional step, and in fact may not be necessary if focused ESWT is initiated first on the patient. Focused ESWT provides inherent properties that acesodyne the targeted anatomical regions and mitigate, sooth or ease any pain and discomfort that may occur during treatment with radial ESWT. As such, if the order of shockwave treatment begins with focused shockwaves, the acesodyne process will negate the need to anesthetize patients in preparation for radial shockwave treatments.

After anesthetizing the patient, if needed, the physician, generally denoted at 146 in FIG. 3, begins the process of using the modality of extracorporeal dual shockwave therapy (ESWT) by applying radial and focused shockwaves to strategic, gender-specific, anatomical regions of the male and female anatomy to treat sexual dysfunction and improve sexual function. The extracorporeal dual shockwave therapy (ESWT) system generally includes a focused and radial shockwave applicator probe 148, 162, having a probe head 150, 160, respectively, where the probes 148, 162 are operatively coupled to respective shockwave generators 154, 158 via an electrical cable 152, 153. Each shockwave generator 154, 158 is disposed on a mobile platform 156 for ease of transporting the ESWT system from place to place within the hospital or medical clinic. Shockwaves are generally high pulses of energy, or continuous transmitted sonic waves or mechanical concussion waves which pass through the surface of the patient's skin to stimulate new blood vessels and new nerve cells to promote the release of cytokines that are associated with removing damaged matrix constituents and promote healing. Dual shockwave therapy includes both radial and focus shockwaves that are applied to patients using the shockwave generator systems 154, 158, as outlined in FIG. 3. A first shockwave generator system 154 is used to apply focus shockwaves to the male and female patient, and then the system 154 is stored away. A second shockwave generator system 158 is then employed to apply radial shockwaves to the male and female patient. With all intended purposes, use of shockwave generator system providing for both radial and focus shockwaves is contemplated if such technological advancement is developed.

Radial and focused shockwaves differ in characteristic and application in terms of magnitude of parameters that involve pressure amplitude, pulse duration, impact, and depth penetration. Radial shockwaves typically comprise about 1 to about 10 bars of pressure, have a pulse duration of about 3 microseconds to about 10 microseconds, provide a radial, divergent pressure field, have a small, superficial penetration depth, and generally affect tissue and close underlying regions of the tissue. Focused shockwaves comprises about 1 to about 10 bars of pressure, have a pulse duration of about 2 microseconds to about 3 microseconds, provide a focused pressure field, have a large penetration depth, and the generally penetrate deeper than radial shockwaves to affect arteries and nerve cells. The pressure bar values identified correlate to the magnitude of pressure of the shockwaves applied. As such, extracorporeal dual shockwave therapy (ESWT) therapy provides radial shockwaves suited for anatomical features located nearer the surface of the skin, while focused shockwaves comprise a smaller focal point for greater accuracy and greater treatment depth targeting anatomical features that are located deeper into a patient's perineal or perineum regions, such as the neurovascular bundle region. Focused shockwaves may be generated by hydroelectric force, or state-of-the-art piezoelectric or electromagnetic systems to provide optimized intensities, focus zones, and long lasting constant dosage outputs. The pulse duration of focused shockwaves is very short, and is generated at low frequencies so it is minimally absorbed by the skin tissue thus resulting in little effects of thermal exposure to the patient skin causing less pain or discomfort, as compared to radial shockwaves which provide a more divergent array of shockwaves to the skin.

With regard to the male patient, as determined in step 122, once the preparation process is complete, and the male patient has been properly instructed on the procedural steps involved in shockwave therapy, a coupling material such as an ultrasound gel, is applied between the anatomical treatment site of the male patient and the wave emanating head 150 of shockwave applicator probe 148 to reduce loss of energy and ensure full transmission and delivery of shockwaves to the underlying anatomical regions during treatment. In step 124, the attending physician begins to apply extracorporeal focused shockwave therapy (F-ESWT) to strategic, gender-specific anatomical target sites, maneuvering the head 150 of the generator probe 148, directly above the strategic regions, as illustrated in the gross anatomical view of the male perineum in FIG. 4. The strategic anatomical areas for applying focused shockwaves in males include the following:

the right and left corpora cavernosa 202, 204 of the penis with a pressure value of about 0.20 to about 0.35 milliJoules per square millimeter ("$mJ/mm^2$")@4 Hz, for about 250 to about 750 pulses each;

the right and left crura 206, 208 of the penis with a pressure value of about 0.20 to about 0.35 $mJ/mm^2$@4 Hz, for about 250 to about 750 pulses each;

the right and left pudendal canal regions 210, 212 of the penis with a pressure value of about 0.20 to about 0.35 $mJ/mm^2$@4 Hz, for about 250 pulses each; and the bulbospongiosis 214 with a pressure value of about 0.20 to about 0.35 $mJ/mm^2$@4 Hz, for about 100 pulses.

Figure 5:
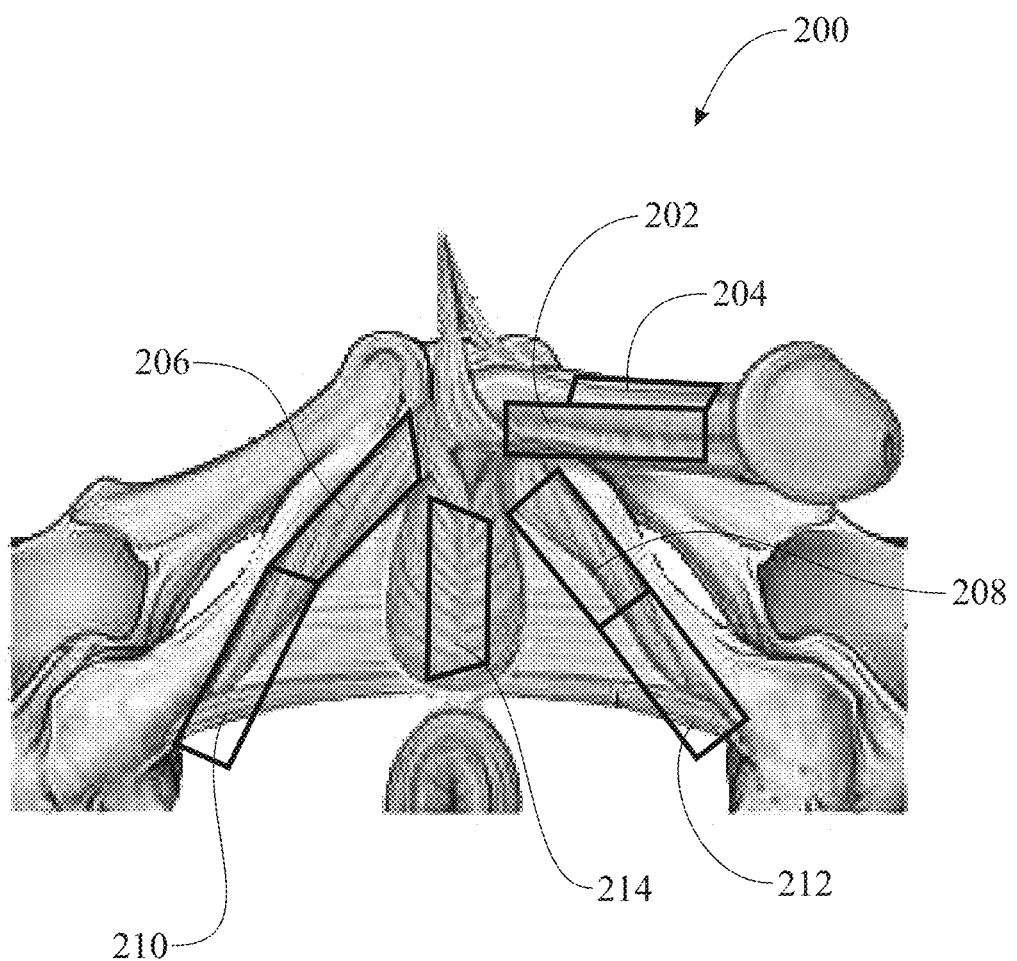
FIG. 5 presents a perineum view of the male genitalia, showing the strategic underlying male anatomical regions receiving the extracorporeal dual shockwave therapy.
Figure 6:
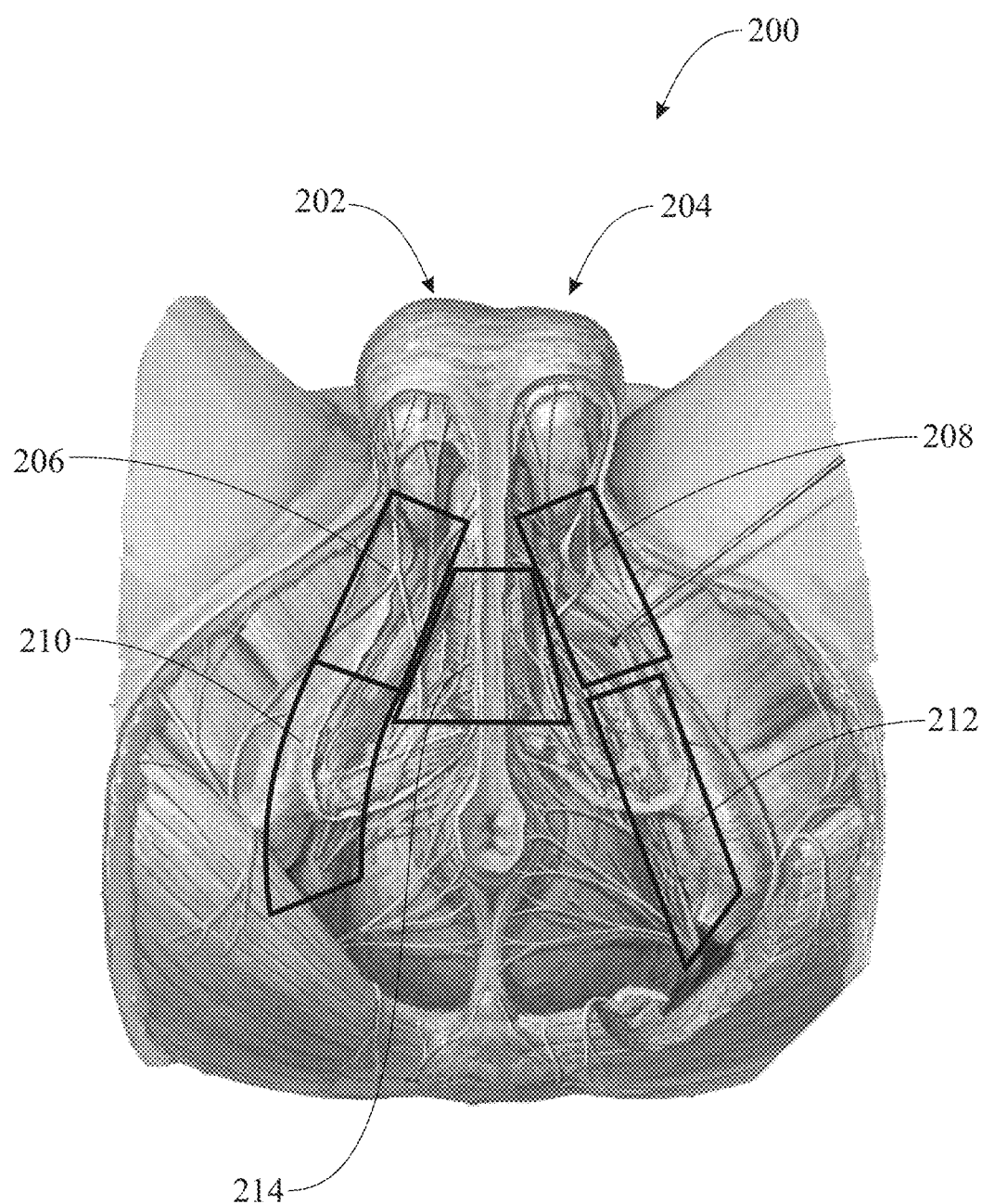
FIG. 6 presents a perineal view of the male genitalia, showing the pudendal and perineal nerve bundle (neurovascular bundle), and the strategic underlying anatomical regions receiving the extracorporeal dual shockwave therapy.

The focus shockwaves penetrate with greater accuracy and to depths reaching the underlying vital anatomical regions 202, 204, 206, 208, 210, 212 and 214, as further illustrated in FIGS. 5 and 6, and stimulate the large area of the penile shaft, and the perineal and pudendal neurovascular bundle. As referenced in FIG. 6, the right and left corpora cavernosa 202, 204, respectively, comprise two large, masses of erectile tissue, or paired vascular spongy organs, that form a large portion of the male penis and which contains most of the blood in the penis during an erection. The right and left crura 206, 208 are each associated with the right left corpora cavernosa 202, 204, respectively, to prevent the erect penis from retracting into the perineum when faced with axial compression load during intercourse. The focused shockwave treatment passes focused shockwaves through the gross anatomical features to penetrate deep into the pudendal neurovascular bundle effectively stimulating the arterial blood vessels, the internal pudendal artery which is a main source of arterial blood supply to the penis, and both pudendal and perineal nerves. As such, the nerves, arteries and veins of the neurovascular bundle are treated with focused shockwaves with specific predetermined pressure magnitudes, frequencies, and number of pulses.

Figure 4:
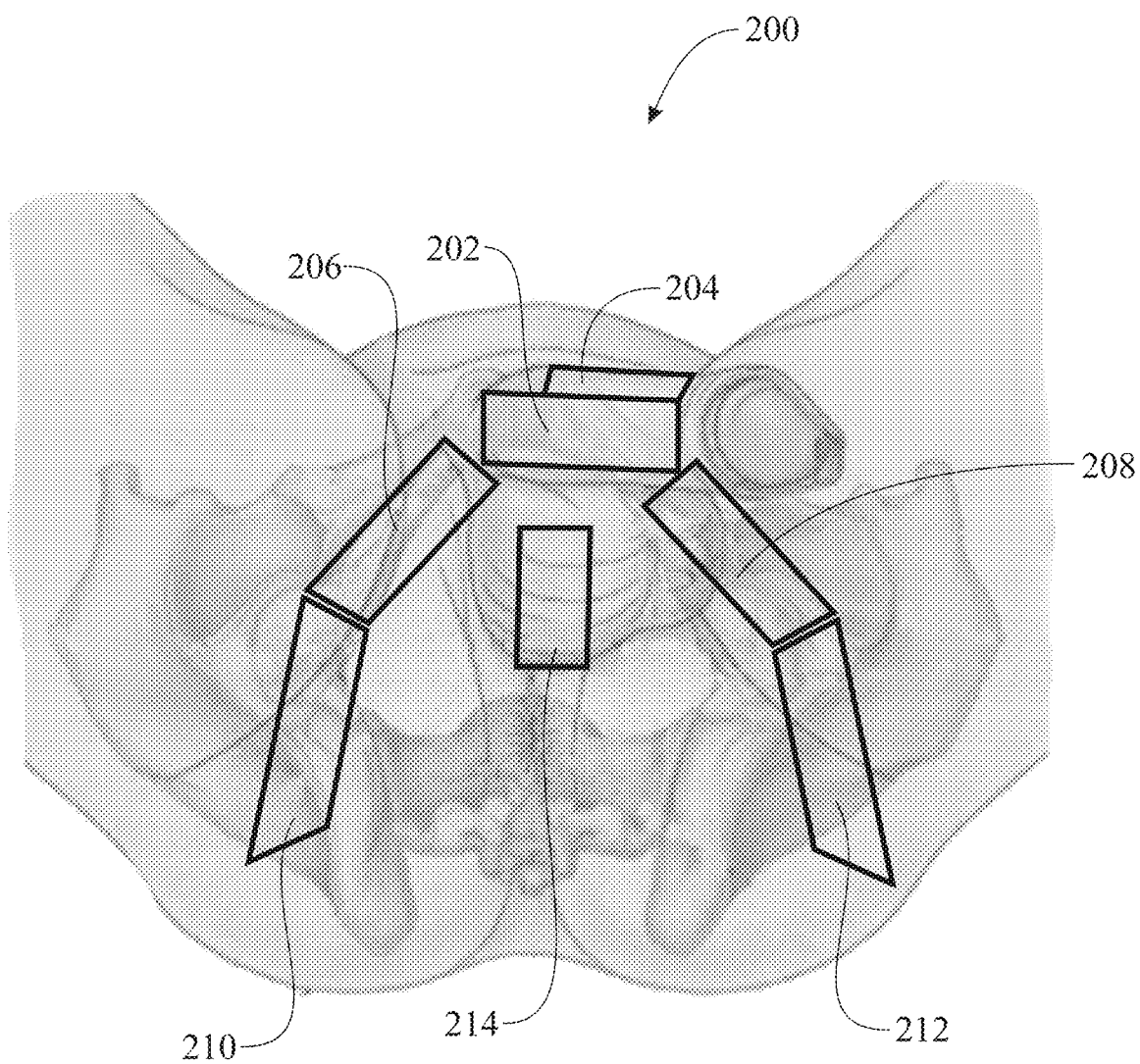
FIG. 4 presents a gross anatomical or superficial perineum view of a male genitalia, showing strategic male anatomical regions for treatment with extracorporeal dual shockwave therapy at prescribed bar values, frequency, and predetermined number of shockwaves.

With continued reference to FIGS. 4 through 6, focused shockwaves are also directed to the anatomical region of the bulbospongiosis, as denoted at 214. In comparison to the other strategic anatomical regions 202, 204, 206, 208, 210 and 212, the number of focus shockwaves attributed to the bulbospongiosis 214 is typically less, generally about 100 pulses. The bulbospongiosis, sometimes referred to as the bulbocavernosus muscle, is a muscle that covers the bulb of the penis and is located in the front of the anus, and innervated by the perineal nerve. The bulbospongiosis 214 aids in the final stages of erection by compressing the veins within the bulb of the penis to maintain tumescence, so acts like a pump that propels sperm out of the body from the prostatic urethra during ejaculation.

With continued approach to the male patient, as determined in step 126, upon completion of the focused shockwaves, the focused shockwave generator 154 is stored away, and the radial shockwave generator 158 is subsequently employed for applying radial shockwaves to the male's strategic anatomical regions, similar to those identified for focused shockwave therapy. Once again, a coupling material such as an ultrasound gel, is applied between the anatomical target site of the male patient and the wave emanating head 160 of shockwave applicator probe 162 to insure adequate energy delivery of radial shockwaves during shockwave treatment. In step 126, the attending physician begins to apply extracorporeal radial shockwave therapy (R-ESWT) to strategic, gender-specific anatomical target sites, maneuvering the head 160 of the generator probe 162 directly above the strategic regions, as illustrated in the gross anatomical view of the male perineum in FIG. 4. The strategic anatomical areas for applying radial shockwaves in males include the following:

the right and left corpora cavernosa 202, 204 of the penis with a pressure value of about 1.7 to about 3.0 bars, which correlates to about 0.15 to about 0.35 mJ/mm$^2$@15 Hz, for about 500 to about 1000 pulses each;

the right and left crura 206, 208 of the penis with a pressure value of about 1.7 to about 3.0 bars, which correlates to about 0.15 to about 0.35 mJ/mm$^2$@15 Hz, for about 500 to about 1000 pulses each;

the right and left pudendal canals region 210, 212 of the penis with a pressure value of about 1.7 to about 3.0 bars, which correlates to about 0.15 to about 0.35 mJ/mm$^2$@15 Hz, for about 1000 pulses each; and the bulbospongiosis 214 with a pressure value of about 1.7 to about 3.0 bars, which correlates to about 0.15 to about 0.35 mJ/mm$^2$@15 Hz, for about 500 pulses.

The stimulating effect of the low-energy, de-focused radial extracorporeal generated shockwaves, pass through the elasticity of tissue as a means to increase local blood circulation, and metabolism in the identified anatomical regions. Radial shockwaves provide a divergent field of shockwave delivery with a superficial penetration depth where shockwave pulses are absorbed more by the tissue, as compared to focused shockwave therapy, thus resulting in more effects of thermal exposure to the patient skin causing more pain or discomfort to patients than focused shockwave therapy. As a result, applying numbing cream or gel to the strategic anatomical regions 202, 204, 206, 208, 210, 212 and 214 of the male anatomy helps elevate discomfort and pain attributed to radial shockwave therapy. The prescribed number of focused shockwaves given to males equates to about 1600 to about 3600 total focused shockwaves per treatment, while the number of radial shockwaves given to males equates to about 4500 to about 6500 pulses total.

In treating female patients for sexual dysfunction, as determined in step 128, each female patient undergoes an initial, preparation process where they are properly instructed on the procedural steps involved in receiving both the radial and focused shockwave therapy. In preparation, the healthcare provider may also apply an anesthetic cream to various anatomical regions including the vulva, clitoral, and anterior vaginal wall regions for prepared contact with the shockwave applicator probes 150, 160 during the dual shockwave treatment process. The female patient is preferably situated in the lithotomy position which entails a supine position with the legs separated, flexed, and supported in raised stirrups, similar to a position sometimes used in childbirth, however, a simple supine position can also be employed. The ultrasound gel is applied between the anatomical target sites of the female patient, and the acoustic wave emanating head 150, 160 of shockwave applicator probe 148, 162, to reduce loss of energy and ensure full transmission of acoustic waves during shockwave treatment. In step 130, the attending physician begins to apply extracorporeal focused shockwave therapy (F-ESWT) to strategic, gender-specific anatomical target sites of the female, maneuvering the head 150 of the generator probe 148, directly above such regions, as illustrated in the gross anatomical view of the female perineum in FIG. 7. The female external genitalia comprise the mons pubis, labia majora, labia minora, clitoris, and vestibule of the vagina, all of which collectively make up the vulva. The strategic anatomical areas of interest for applying focused shockwaves in females include the following:

the corpora of clitoris 302, 304 of the vagina with a pressure value of about 0.25 mJ/mm$^2$@4 Hz, for about 100 pulses each;

the right and left side crura 306, 308 (over the labia majora sections) with a pressure value of about 0.25 to about 0.35 mJ/mm$^2$@4 Hz, for about 250 to about 500 pulses each;

the right and left side labia minora sections 310, 312 (over the pudendal canals) with a pressure value of about 0.25 to about 0.35 mJ/mm$^2$@4 Hz, for about 250 to about 500 pulses each:

the anterior vaginal wall 314 or the entire interior circumference of the distal vaginal canal with a pressure value of about 0.20 to about 0.40 mJ/mm$^2$@4 Hz, for about 300 to about 500 pulses; and the median raphe and perineum 316 with a pressure value of about 0.20 to about 0.35 mJ/mm$^2$@4 Hz, for about 300 to about 500 pulses.

Figure 7:
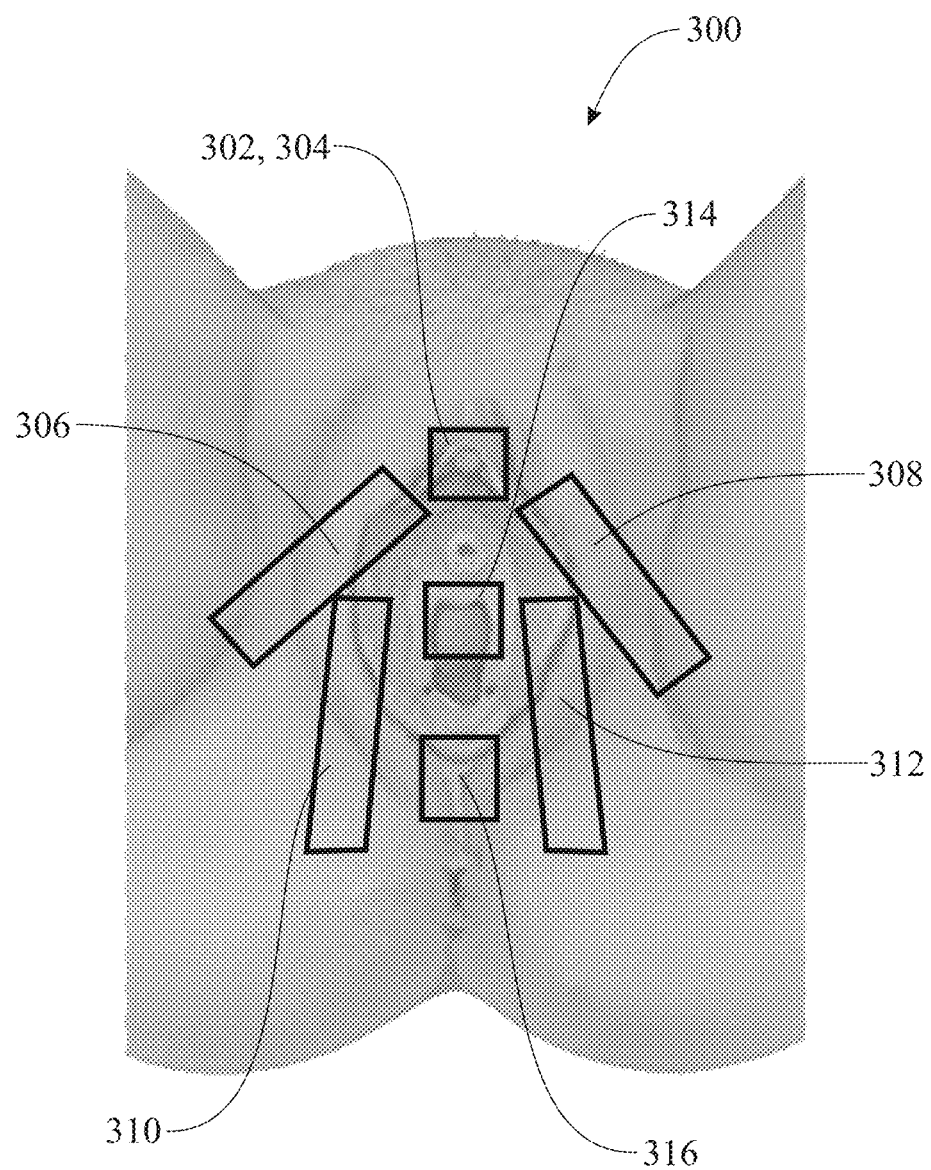
FIG. 7 presents a gross anatomical or superficial perineum view of a female genitalia, showing strategic female anatomical regions for treatment with extracorporeal dual shockwave therapy at prescribed bar values, frequency, and predetermined number of shockwave pulses.
Figure 8:
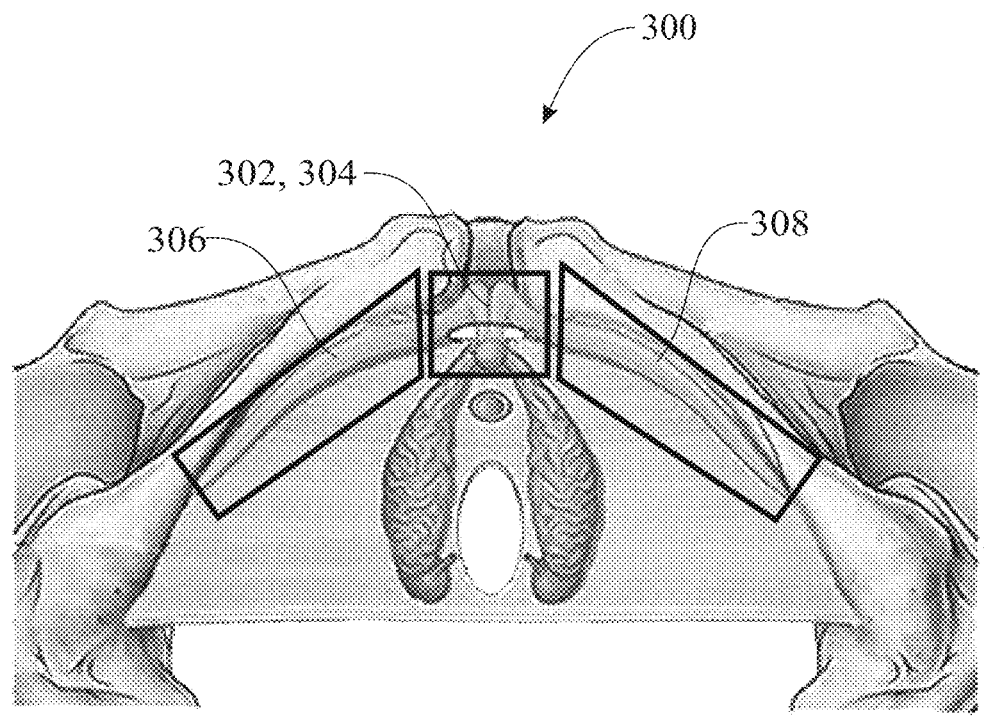
FIG. 8 presents a perineum view of the female genitalia, showing the strategic underlying female anatomical regions receiving the extracorporeal dual shockwave therapy.

The focused shockwaves penetrate below the gross anatomical skin of the corpora of clitoris 302, 304 regions, and labia majora regions 306, 308, of the female patient, as shown in FIG. 7, to treat the underlying areas of the clitoral gland, corpus cavernosum, and crus of clitoris, as illustrated by elements 302, 304, 306 and 308 in FIG. 8. As shown in FIG. 8, the clitoris regions are attached to, and extend along, the pelvic bone. The labia majora regions 306, 308 are fleshy folds of fat tissue that extend downwards along opposite sides surrounding, the vaginal and urethral orifices. The labia major regions 306, 308 contain fat, sweat and oil glands, and are homologous to the male scrotum. The labia minora regions 310, 312, are folds of smooth tissue that include oil glands and pressure receptors, but no sweat glands. The labia minor regions 310, 312 underlie the labia majora regions 306, 308, respectively. The median raphe and perineum 316 is generally a strip of tissue that extends from the anus to the opening of the vagina of the female.

Figure 9:
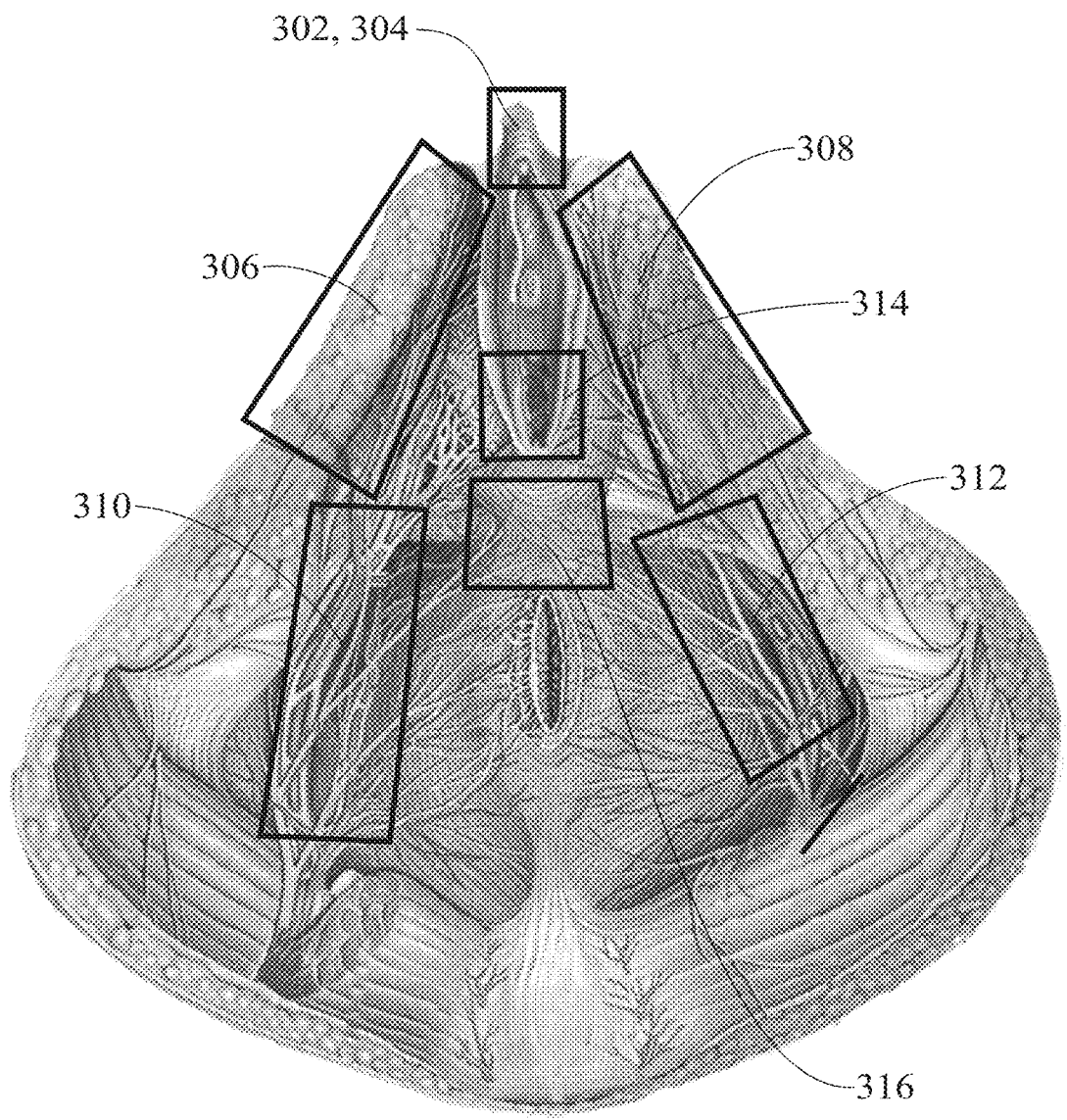
FIG. 9 presents a perineal view of the female genitalia, showing the pudendal and perineal nerve bundle (neurovascular bundle), and the strategic underlying anatomical regions receiving extracorporeal dual shockwave therapy.

The head 150 of the focused shockwave probe 148 is applied over the female patient's skin, directly over the strategic anatomical regions 302, 304, 306, 308, 310, 312, 314 and 316 to effectually disperse extracorporeal focused shockwaves that penetrate at greater accuracy, and deeper in depth, reaching the underlying vital anatomical regions 302, 304, 306, 308, 310, 312, 314 and 316 of the female, including pudendal canals of the perineal or pudendal neurovascular bundle, as shown in FIG. 9. The focused shockwaves stimulate and promote blood circulation in the arteries, veins, and nerves of the female's neurovascular bundle regions associated with the labia majora 306, 308, and the labia minor 310, 312. It will be understood that when applying focused shockwaves to the anterior vaginal wall 314, a polymeric cover can be inserted over the head 150 of the probe 148, and the head 150 carefully inserted into the vaginal canal during treatment. The median raphe and perineum 316 is generally a strip of tissue that extends from the anus to the opening of the vagina of the female. This area is also treated with focus shockwave therapy for a predetermined number of shockwaves.

With continued therapy, in step 132, the focused shockwave generator 154 is stored away, and a radial shockwave generator 158 is employed for applying radial shockwaves to the same strategic anatomical regions 302, 304, 306, 308, 310, 312, 314 and 316 of the female. A coupling ultrasound gel, is applied between the anatomical target site of the patient and the radial wave emanating head 160 of shockwave applicator probe 162 to reduce loss of energy and ensure full transmission of acoustic waves during radial shockwave treatment. In step 132, the attending physician begins to apply extracorporeal radial shockwave therapy (R-ESWT) to strategic, gender-specific anatomical target sites, maneuvering the head 160 of the generator probe 162, directly above the strategic regions, as illustrated in the gross anatomical view of the female perineum in FIG. 7. The strategic anatomical areas for applying radial shockwaves in female patients include the following:

the corpora of clitoris 302, 304 of the vagina with a pressure value of about 1.7 to about 3.0 bars, which correlates to about 0.15 to about 0.35 mJ/mm$^2$@15 Hz, for about 250 pulses;

the right and left side crura 306, 308 (over the labia majora sections) with a pressure value of about 1.7 to about 3.0 bars, which correlates to about 0.15 to about 0.35 mJ/mm$^2$@15 Hz, for about 500 to about 1000 pulses each;

the right and left side labia minora sections 310, 312 (over the pudendal canals) with a pressure value of about 1.7 to about 3.0 bars, which correlates to about 0.15 to about 0.35 mJ/mm$^2$@15 Hz, for about 1000 pulses each;

the anterior vaginal wall 314 or the entire interior circumference of the distal vaginal canal with a pressure value of about 1.7 to about 3.0 bars, which correlates to about 0.15 to about 0.35 mJ/mm$^2$@15 Hz, for about 1000 pulses; and the median raphe and perineum 316 with a pressure value of about 1.7 to about 3.0 bars, which correlates to about 0.15 to about 0.35 mJ/mm$^2$@15 Hz, for about 250 pulses.

The stimulating effect of the low-energy, defocused radial extracorporeal generated shockwaves pass through the elasticity of tissue as a means to increase local blood circulation, and metabolism in the strategic areas identified. The radial shockwaves reflect back under close proximity to the skin, and do not penetrate deep in the underlying anatomy as with the focused shockwaves. As before, the application of the combination of focused and radial shockwave treatments as outlined above for both male and female patients comprise a single treatment session. Additional treatment sessions provided to the male and female patient are governed by the severity of the sexual dysfunction as illustrated in steps 110, 112 and 114 of FIG. 1A. Thus, for example, if a patient's sexual dysfunction is deemed to be moderate, there are up to 6 treatments of both focused and radial shockwave treatments that will be needed. The 6 treatments may be given three times a week for 2 weeks, or twice a week for 3 weeks, or once a week for 6 weeks. The exact number of treatments and/or sessions, and the time period determined in given such dual shockwave treatments is determined in advance by the attending physician, and also adjusted over time by the attending physician as well.

The bar or measured pressure values, frequency delivered, and number of pulses applied, in dual shockwave therapy treatments, may be adjusted at any time, before or during the course of a treatment session, to deliver the focused and radial shockwaves needed to effectively treat males suffering from erectile dysfunction, and females suffering from sexual dysfunction. The prescribed bar values or energy flux density values, delivery frequency, and number of pulse applied, are predetermined based on the severity of the sexual dysfunction, and the amount of tissue stimulation a patient can tolerate during the dual shockwave procedure without patients experiencing high levels of pain or discomfort. As such, delivery of both focused and radial shockwaves, may comprises shockwaves having a variety of different frequencies, for example, from about 2 Hz to about 18 Hz, pressure bar values may be from about 1.5 to about 4 bars. (or corresponding energy flux density values in mJ/mm$^2$), and a total number of pulses from about 4500 to about 6500 for radial shockwaves, and about 1600 to about 3600 for focused shockwaves. The attending physician may begin the dual shockwave therapy in any order, and may start off with a high frequency and low pressure value, and then gradually lower the frequency while gradually raising the bar value or pressure values during the treatment process. The bar value may be titrated over a period of time to determine the patient's tolerance threshold, and to determine what bar value, or range of frequency or both, that is most effective in treating the male and/or female patient. Upon reaching such determined values or ranges of values, the attending physician may program each shockwave generator 154, 158 to deliver the dual shockwaves at the predetermined frequency and bar values for any subsequent treatments.

Upon completion, both male and female patients are given a cloth or towel to wipe off any ultrasonic gel, and/or numbing cream remaining on the surface of the skin. In some situations, the male patients may prefer to clean up the water, soluble, non-staining ultrasound gel themselves. In steps 134, 136 of FIG. 2, the attending physician reviews the process and treatments and determines whether the dual shockwave treatment should be repeated, and if so, the process of delivering dual shockwave therapy begins over at steps 120.

In steps 138, 140 of FIG. 2, upon completing dual shockwave therapy, the male and female patients are given instructions regarding post treatment follow-up, medications, and other medical care management. In most cases, the dual shockwave of focused and radial therapy imposes no restrictions on sexual activity and patients are instructed that they may resume sexual activity. Patients are advised to keep a close eye on treated regions for any adverse reactions, such as skin irritation, burns, blisters, or whether they experience ongoing discomfort or pain. Patients are instructed that some residual soreness may occur or linger for a few hours in the anatomical, target regions. Patients are reassured that signs of excoriations will heal promptly, and to avoid using anti-inflammatory medications such as ibuprofen, or aspirin, but rather, to use alternative medications, such as acetaminophen or opiates for discomfort or pain. In some circumstances, attending physicians may prescribe NEO40 lozenges, 2 daily plus or minus, recommend tadalafil 5 mg daily, or other medicines that help heal or better tolerate discomfort. In step 140, patients are instructed to return to the clinic for continued radial and shockwave therapy treatment after 6 to 7 days of rest.

Post-treatment procedures encourage males and females to undergo a variety of traction and stimulation exercises. Traction exercises in male patients may include the use of a penile vacuum pump that is employed to induce erection in the penis. The penile vacuum pump typically includes a receptacle for inserting the penis where the receptacle is associated with a vacuum pump that is operated to create a suction or vacuum in the receptacle. The penis is inserted within the receptacle, and the pump mechanism is compressed by hand to generate an internal vacuum within the receptacle to induce erection. The penile pump traction may be used a set number of times per day, or weekly, for a predetermined amount of time, such as ten minutes on each occasion. Female patients are also encouraged to engage in stimulation exercises. Female stimulation exercises may include the use of a vibrator, clitoral stimulator, prosthetic penis, or other sexual appliance or aid that may is used a set number of times daily, or as needed.

Dual shockwave therapy is prescribed when conventional methods of treatment are not effective in treating erectile dysfunction in men and sexual dysfunction in women, to improve sexual function. However, a variety of complementary therapies can be used in addition to dual shockwave therapy. For example, dual shockwave therapy may be used in conjunction with, or in addition to, peptide therapy, PT141, mainly to observe reaction and monitor response, with platelet-rich plasma (PRP) therapy, in which blood plasma is enriched with platelets, O-shot and P-shot with exosomes, with exosomes and PRP, with phosphodiesterase type 5 inhibitors (PDE5I), with testosterone replacement therapy, with estrogen/androgen therapy, with intra-cavernosal injections, and/or with any combination thereof.

The extracorporeal dual shockwave therapy of both focused and radial shockwaves are generally represented in bar values, delivery frequency of shockwaves, and the number of shockwave pulses given. Such bar values may correlate to energy flux density values which refers to the measure of energy per square area that is being released by the sonic pulses at a specific finite point, or a rate of transfer of energy through a surface, and can be computed as an area below the squared pressure time curve. Energy flux density correlates to the maximum amount of acoustical energy that is transmitted in an area 1 square millimeter per pulse, and is generally represented in $mJ/mm^2$ where (mJ) represents energy measurement in milliJoules. Thus, dual shockwave therapy for both focused and radial shockwaves may employ energy flux density values that correlate to predetermined bar values referenced herein, and/or deemed effective for treating erectile and sexual dysfunction in males and females, without departing from the scope of the invention.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A method for treating a patient suffering from an erectile dysfunction or a sexual dysfunction, said method comprising:
    evaluating the patient to determine an initial level of severity of the erectile dysfunction or the sexual dysfunction of the patient;
    targeting at least one strategic anatomical region of the penis or the vagina of the patient to receive treatment;
    determining a number of treatments to be applied to the at least one strategic anatomical region targeted;
    developing a focused extracorporeal shockwave therapy treatment regimen defining at least a focused extracorporeal shockwave therapy pressure and frequency, and a number of focused extracorporeal shockwave therapy pulses per treatment to be applied to the at least one strategic anatomical region targeted;
    developing a radial extracorporeal shockwave therapy treatment regimen defining at least a radial extracorporeal shockwave therapy pressure and frequency, and a number of radial extracorporeal shockwave therapy pulses per treatment to be applied to the at least one strategic anatomical region targeted;
    exposing the at least one strategic anatomical region of the patient targeted to the number of focused extracorporeal shockwave therapy pulses at the focused extracorporeal shockwave therapy pressure and frequency from a focused extracorporeal shockwave generator; and
    exposing the at least one strategic anatomical region of the patient targeted to the number of radial extracorporeal shockwave therapy pulses at the radial extracorporeal shockwave therapy pressure and frequency from a radial extracorporeal shockwave generator.

2. The method as recited in claim 1 wherein the at least one strategic anatomical region targeted is selected from the group consisting of the right or left corpora cavernosa, the right or left crura, the right or left pudendal canal regions, and the bulbospongiosis of the patient's penis.

3. The method as recited in claim 2 wherein the focused extracorporeal shockwave therapy treatment regimen is at least partially defined by a focused extracorporeal shockwave therapy pressure of about 0.20 to about 0.35 milliJoules per square millimeter at a frequency of about 4 Hertz.

4. The method as recited in claim 3 wherein the focused extracorporeal shockwave therapy treatment regimen is further defined by a number of focused extracorporeal shockwave therapy pulses of about 100 to about 750 per treatment to be applied to the at least one strategic anatomical region targeted.

5. The method as recited in claim 2 wherein the radial extracorporeal shockwave therapy treatment regimen is at least partially defined by a radial extracorporeal shockwave therapy pressure of about 0.15 to about 0.35 milliJoules per square millimeter at a frequency of about 15 Hertz.

6. The method as recited in claim 5 wherein the radial extracorporeal shockwave therapy treatment regimen is further defined by a number of radial extracorporeal shockwave therapy pulses of about 500 to about 1000 per treatment to be applied to the at least one strategic anatomical region targeted.

7. The method as recited in claim 1 the at least one strategic anatomical region targeted is selected from the group consisting of the corpora of the clitoris, the right or left crura over the labia majora sections, the right or left labia minora sections over the pudendal canals, the anterior vaginal wall, and the median raphe and perineum of the patient's vagina.

8. The method as recited in claim 7 wherein the focused extracorporeal shockwave therapy treatment regimen is at least partially defined by a focused extracorporeal shockwave therapy pressure of about 0.20 to about 0.40 milliJoules per square millimeter at a frequency of about 4 Hertz.

9. The method as recited in claim 8 wherein the focused extracorporeal shockwave therapy treatment regimen is further defined by a number of focused extracorporeal shockwave therapy pulses of about 100 to about 500 per treatment to be applied to the at least one strategic anatomical region targeted.

10. The method as recited in claim 7 wherein the radial extracorporeal shockwave therapy treatment regimen is at least partially defined by a radial extracorporeal shockwave therapy pressure of about 0.15 to about 0.35 milliJoules per square millimeter at a frequency of about 15 Hertz.

11. The method as recited in claim 10 wherein the radial extracorporeal shockwave therapy treatment regimen is further defined by a number of radial extracorporeal shockwave therapy pulses of about 250 to about 1000 per treatment to be applied to the at least one strategic anatomical region targeted.

12. The method as recited in claim 1 wherein the number of treatments will be about 1 to 3 wherein the initial level of severity of the erectile dysfunction or the sexual dysfunction of the patient is mild.

13. The method as recited in claim 1 wherein the number of treatments will be about 3 to 6 wherein the initial level of severity of the erectile dysfunction or the sexual dysfunction of the patient is moderate.

14. The method as recited in claim 1 wherein the number of treatments will be about 6 to 12 wherein the initial level of severity of the erectile dysfunction or the sexual dysfunction of the patient is severe.

15. A method for treating a patient suffering from an erectile dysfunction or a sexual dysfunction, said method comprising:
   evaluating the patient to determine an initial level of severity of the erectile dysfunction or the sexual dysfunction of the patient;
   targeting a plurality of strategic anatomical regions of the penis or the vagina of the patient to receive treatment, based at least in part on the level of severity of the erectile dysfunction or the sexual dysfunction of the patient;
   determining a number of treatments to be applied to each of the plurality of strategic anatomical regions targeted, based at least in part on the level of severity of the erectile dysfunction or the sexual dysfunction of the patient;
   developing a radial extracorporeal shockwave therapy treatment regimen defining at least a predetermined radial extracorporeal shockwave therapy pressure and frequency, and a predetermined number of radial extracorporeal shockwave therapy pulses per treatment to be applied to each of the plurality of strategic anatomical regions targeted, based at least in part on the level of severity of the erectile dysfunction or the sexual dysfunction of the patient;
   developing a focused extracorporeal shockwave therapy treatment regimen defining at least a predetermined focused extracorporeal shockwave therapy pressure and frequency, and a predetermined number of focused extracorporeal shockwave therapy pulses per treatment to be applied to each of the plurality of strategic anatomical regions targeted, based at least in part on the level of severity of the erectile dysfunction or the sexual dysfunction of the patient;
   applying a coupling material between each of the plurality of strategic anatomical regions targeted to receive treatment and a radial wave emanating head of a radial extracorporeal shockwave generator;
   exposing each of the plurality of strategic anatomical regions targeted to the predetermined number of radial extracorporeal shockwave therapy pulses at the predetermined radial extracorporeal shockwave therapy pressure and frequency from the radial extracorporeal shockwave generator;
   applying a coupling material between each of the plurality of strategic anatomical regions targeted to receive treatment and a focused wave emanating head of a focused extracorporeal shockwave generator; and
   exposing each of the plurality of strategic anatomical regions targeted to the predetermined number of focused extracorporeal shockwave therapy pulses at the predetermined focused extracorporeal shockwave therapy pressure and frequency from the focused extracorporeal shockwave generator.

16. The method as recited in claim 15 wherein the focused extracorporeal shockwave therapy treatment regimen is at least partially defined by a focused extracorporeal shockwave therapy pressure of about 0.20 to about 0.40 milliJoules per square millimeter at a frequency of about 4 Hertz.

17. The method as recited in claim 16 wherein the focused extracorporeal shockwave therapy treatment regimen is further defined by a number of focused extracorporeal shockwave therapy pulses of about 100 to about 750 per treatment to be applied to each of the plurality of strategic anatomical regions targeted.

18. The method as recited in claim 17 wherein the radial extracorporeal shockwave therapy treatment regimen is at least partially defined by a radial extracorporeal shockwave therapy pressure of about 0.15 to about 0.35 milliJoules per square millimeter at a frequency of about 15 Hertz.

19. The method as recited in claim 18 wherein the radial extracorporeal shockwave therapy treatment regimen is further defined by a number of radial extracorporeal shockwave therapy pulses of about 250 to about 1000 per treatment to be applied to each of the plurality of strategic anatomical regions targeted.

20. A method for treating a patient suffering from an erectile dysfunction or a sexual dysfunction, said method comprising:
   evaluating the patient to determine an initial level of severity of the erectile dysfunction or the sexual dysfunction of the patient;
   targeting a plurality of strategic anatomical regions of the penis or the vagina of the patient to receive treatment, based at least in part on the level of severity of the erectile dysfunction or the sexual dysfunction of the patient;
   determining a number of treatments to be applied to each of the plurality of strategic anatomical regions targeted, based at least in part on the level of severity of the erectile dysfunction or the sexual dysfunction of the patient, wherein the number of treatments will be about 1 to 3 wherein the initial level of severity of the erectile dysfunction or the sexual dysfunction of the patient is mild, the number of treatments will be about 3 to 6 wherein the initial level of severity of the erectile dysfunction or the sexual dysfunction of the patient is moderate, and the number of treatments will be about 6 to 12 wherein the initial level of severity of the erectile dysfunction or the sexual dysfunction of the patient is severe;
   developing a radial extracorporeal shockwave therapy treatment regimen defining at least a predetermined radial extracorporeal shockwave therapy pressure and a predetermined number of radial extracorporeal shockwave therapy pulses per treatment to be applied to each of the plurality of strategic anatomical regions targeted, based at least in part on the level of severity of the erectile dysfunction or the sexual dysfunction of the patient;
   developing a focused extracorporeal shockwave therapy treatment regimen defining at least a predetermined focused extracorporeal shockwave therapy pressure and a predetermined number of focused extracorporeal shockwave therapy pulses per treatment to be applied to each of the plurality of strategic anatomical regions targeted, based at least in part on the level of severity of the erectile dysfunction or the sexual dysfunction of the patient;
   applying a coupling material between each of the plurality of strategic anatomical regions targeted to receive treatment and a focused wave emanating head of a focused shockwave applicator probe of a focused extracorporeal shockwave generator;
   exposing each of the plurality of strategic anatomical regions targeted to the predetermined number of focused extracorporeal shockwave therapy pulses at the predetermined focused extracorporeal shockwave therapy pressure from the focused extracorporeal shockwave generator;

applying a coupling material between each of the plurality of strategic anatomical regions targeted to receive treatment and a radial wave emanating head of a radial shockwave applicator probe of a radial extracorporeal shockwave generator;

exposing each of the plurality of strategic anatomical regions targeted to the predetermined number of radial extracorporeal shockwave therapy pulses at the predetermined radial extracorporeal shockwave therapy pressure from the radial extracorporeal shockwave generator; and evaluating the patient to determine a post treatment level of severity of the erectile dysfunction or the sexual dysfunction of the patient.

\* \* \* \* \*